United States Patent
Thakashinamoorthy et al.

(10) Patent No.: US 7,329,756 B2
(45) Date of Patent: Feb. 12, 2008

(54) PROCESS FOR THE MANUFACTURE OF ISRADIPINE

(75) Inventors: Chandiran Thakashinamoorthy, Tamil Nadu (IN); Minor Kumar Senthil, Tamil Nadu (IN); Kaliyaperumal Palanivel, Tamil Nadu (IN); Radhakrishnan Selvaraju Mullaiyur, Tamil Nadu (IN)

(73) Assignee: Shasun Chemicals and Drugs Limited, Chennai (IN)

( * ) Notice: Subject to any disclaimer, the term of this patent is extended or adjusted under 35 U.S.C. 154(b) by 123 days.

(21) Appl. No.: 10/564,804

(22) PCT Filed: Jul. 15, 2004

(86) PCT No.: PCT/IN2004/000208

§ 371 (c)(1),
(2), (4) Date: Jan. 13, 2006

(87) PCT Pub. No.: WO2005/005437

PCT Pub. Date: Jan. 20, 2005

(65) Prior Publication Data

US 2006/0167063 A1  Jul. 27, 2006

(30) Foreign Application Priority Data

Jul. 15, 2003 (IN) .......................... 571/CHE/2003

(51) Int. Cl.
*C07D 413/04* (2006.01)
(52) U.S. Cl. .................................................. 546/269.4
(58) Field of Classification Search .............. 546/269.4
See application file for complete search history.

(56) References Cited

U.S. PATENT DOCUMENTS 4,466,972 A  8/1984 Neumann

*Primary Examiner*—Patricia L. Morris
(74) *Attorney, Agent, or Firm*—Knobbe Martens Olson & Bear LLP

(57) ABSTRACT

The present invention relates to an improved method for the manufacture of Isradipine, 4-(4-Benzofurazanyl)-1,4-dihydro-2,6-dimethyl-3,5-pyridinedicarboxylic acid methyl 1-methylethyl ester. Which, involves reacting 2,1,3-benzoxadiazole-4-carboxaldehyde with methyl acetoacetate in the presence of acetic acid and piperidine in diisopropyl ether. To obtain the product 2-acetyl-3-benzofurazan-4-yl-acrylic acid methyl ester which is then reacted with isopropyl-β-aminocrotonate in ethanol at 25 to 35° C. to obtain the product.

11 Claims, No Drawings

PROCESS FOR THE MANUFACTURE OF ISRADIPINE

This application is a National Stage entry under 35 U.S.C. § 371 of International Application No. PCT/IN2004/000208, filed Jul. 15, 2004, which was published in English, designated the U.S., and claims priority to India Patent Application No. 571/Che/2003, which was filed Jul. 15, 2003, both of which are incorporated herein by reference in their entireties.

FIELD OF THE INVENTION

The present invention relates to an improved method for the manufacture of Isradipine, 4-(4-Benzofurazanyl)-1,4-dihydro-2,6-dimethyl-3,5-pyridinedicarboxylic acid methyl 1-methylethyl ester. More particularly the present invention relates to the process for the manufacture of Isradipine of substantially high purity and relatively free from the symmetrical ester impurities.

BACKGROUND OF THE INVENTION

Isradipine is 4-(4-Benzofurazanyl)-1,4-dihydro-2,6-dimethyl-3,5-pyridinedicarboxylic acid methyl 1-methylethyl ester having the chemical structure of formula (I).

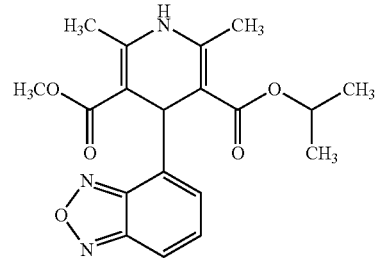

(I)

Isradipine is therapeutically indicated for treating cardiovascular diseases. The cardiovascular diseases include angina, pectoris, hypertension and congestive heart failure. It is also used to treat high blood pressure.

Isradipine was disclosed in the German specification DE 2949491 and U.S. Pat. Nos. 4,466,972 and 4,567,271. DE 2949491 describes the general procedure to prepare 1,4-dihydropyridine derivatives. U.S. Pat. No. 4,466,972, GB02103203A, LU 0088342A9, EP 0000150A1, EP 0000150B1, AU 0538515B2 and other related patents describe the general method for the preparation of Benzoxadiazoles and their derivatives of general formula (II). These references in its entirety is hereby incorporated by reference into this application.

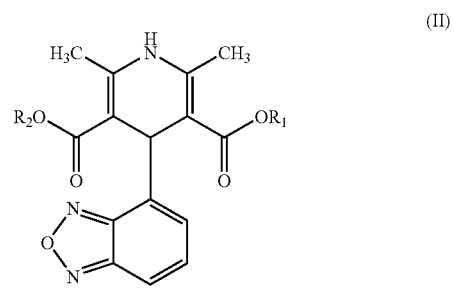

(II)

Where in $R_1$ is —$CH_3$ and $R_2$ is —$CH(CH_3)_2$ it refers to Isradipine of formula (I). When $R_1$ and $R_2$ are not identical the general procedures described in these patent specifications produces a mixture of isomers of formula (II). These procedures for the preparation of Isradipine is characteristic of formation of the isomeric impurities, 1) 4-(4-Benzofurazanyl)-1,4-dihydro-2,6-dimethyl-3,5-pyridinedicarboxylic acid di-methyl ester of formula (III) and 2) 4-(4-Benzofurazanyl)-1,4-dihydro-2,6-dimethyl-3,5-pyridinedicarboxylic acid di-1-methylethyl ester of formula (IV) along pith Isradipine.

The U.S. Pat. No. 4,466,972 describes the preparation of compounds of general formula (II) by refluxing 2, 1, 3-benzoxadiazole-4-carboxaldehyde, keto ester and concentrated ammonia or a β-amino ester in presence of ethanol, followed by evaporation and purification by chromatography.

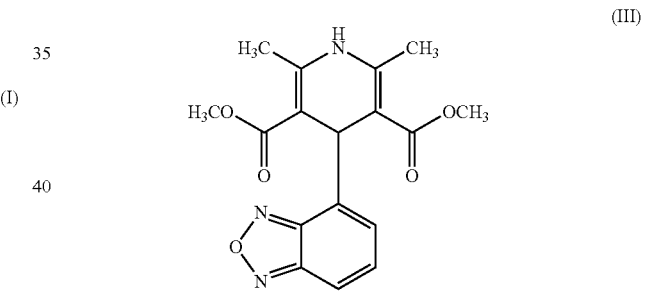

(III)

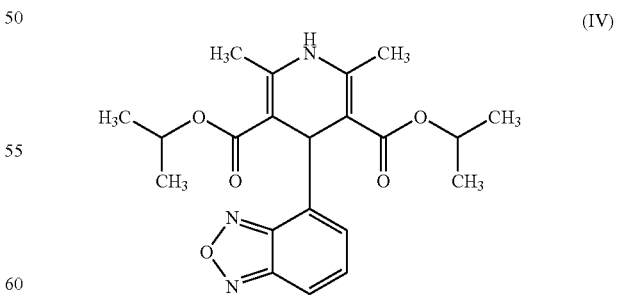

(IV)

These symmetrical ester isomers (III) and (IV) are difficult to separate from the Isradipine and the separation is effected only by a chromatographic purifications. The drawback with the procedures described in these patents is that it is very difficult to produce the product in commercial quantities as it involves the purification of the product by chromatographic separations.

A single step process for the preparation of Isradipine was described in CH 661270. This procedure involves first reacting 2,1,3-benzoxadiazole-4-carboxaldehyde with isopropyl acetoacetate in the presence of catalytic quantities of acetic acid and piperidine in refluxing toluene, and further reacting it with methyl-β-aminocrotonate. The Isradipine formed in the reaction mixture was then. separated by toluene distillation followed by cyclohexane treatment. The crude product obtained was then crystallised from ethanol to get Isradipine. When we have repeated this process in our laboratory we got the Isradipine with substantially higher amount of symmetrical ester isomers (III) and (IV) are present in the product. Removal of these symmetrical ester isomers is very difficult even after several repurifications from ethanol.

OBJECTS OF THE INVENTION

The object of the present invention is to provide an improved method for the manufacture of Isradipine, 4-(Benzofuranzayl)-1,4-dihydro-2,6-dimethyl-3,5-pyridine dicarboxylic acid methyl-1-methylethyl ester.

It is a further object of the instant invention to obtain Isradipine of substantially high purity and relatively free from the symmetrical ester impurities, capable of being used to product commercial quantities of Isradipine pharmaceutical grade.

SUMMARY OF THE INVENTION

To achieve the afore-mentioned objects, the present invention provides for a process for the manufacture of the Isradipine which, involves two steps. In the first step 2,1,3-benzoxadiazole-4-carboxaldehyde is reacted with methyl acetoacetate in the presence of acetic acid and piperidine in diisopropyl ether. The product 2-acetyl-3-benzofurazan-4-yl-acrylic acid methyl ester is isolated and purified to get substantially high purity product with less than 0.3% 2,1,3-benzoxadiazole-4-carboxaldehyde content present in the purified product. In the second step the purified intermediate 2-acetyl-3-benzofurazan-4-yl-acrylic acid methyl ester is reacted with isopropyl-β-aminocrotonate in ethanol at 25 to 35° C. The crude Isradipine is crystallised from ethanol to get pure Isradipine having substantially higher purity and containing lower amount of the symmetrical ester isomers (III) and (IV).

DETAILED DESCRIPTION OF THE INVENTION

The present invention relates to an improved method for the manufacture of Isradipine, 4-(4-Benzofurazanyl)-1,4-dihydro-2,6-dimethyl-3,5-pyridinedicarboxylic acid methyl 1-methylethyl ester. More particularly the present invention relates to the process for the manufacture of Isradipine of substantially high purity and relatively free from the symmetrical ester impurities.

The present process for the manufacture of the Isradipine involves two steps. The following scheme 1 illustrates a reaction sequence of the present invention for the manufacture of the Isradipine.

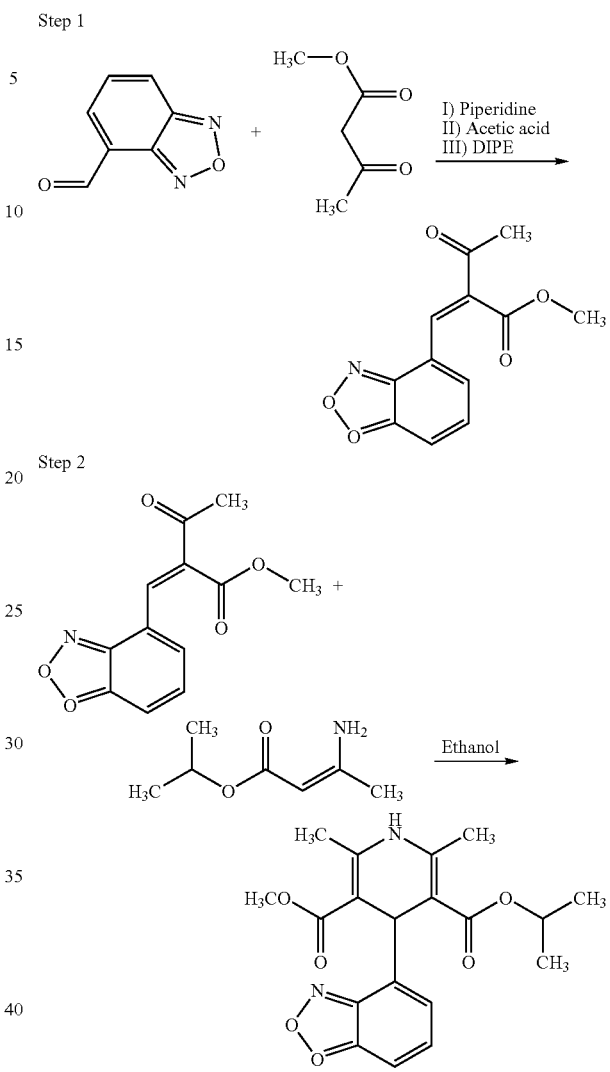

In the first step, 2,1,3-benzoxadiazole-4-carboxaldehyde is reacted with methyl acetoacetate in the presence of acetic acid and piperidine in diisopropyl ether. The reaction is carried out in diisopropyl ether under reflux with simultaneous removal of water formed during the reaction. Removal of the water from the reaction mixture enables the reaction to proceed at a faster rate. The reaction is completed at the end of theoretical amount of water removal from the reaction mixture. The completion of the reaction is determined by qualitative HPLC analysis. In this reaction methyl acetoacetate 0.9 to 1.1 mol is used for every 1.0 mol of 2,1,3-benzoxadiazole-4-carboxaldehyde, preferably 0.95 to 1.0 mol methyl acetoacetate is used for every 1.0 mol of 2,1,3-benzoxadiazole-4-carboxaldehyde. Acetic acid and piperidine are used in catalytic amount, preferably acetic acid 0.25 to 0.30 mol and piperidine 0.08 to 0.06 mol is used for every 1.0 mol of 2,1,3-benzoxadiazole-4-carboxaldehyde. This reaction goes to completion after 8 to 12 hr at reflux. The reaction mixture is then washed with dilute hydrochloric acid, followed by dilute sodium bicarbonate solution and followed by water. The crude product 2-acetyl-3-benzofurazan-4-yl-acrylic acid methyl ester is then obtained by distillation of diisopropyl ether under vacuum.

The crude product is then crystallised from diisopropyl ether to get the pure 2-acetyl-3-benzofurazan-4-yl-acrylic acid methyl ester having purity more than 99% (both cis and trans isomers), and it contained less than 0.3% 2,1,3-benzoxadiazole-4-carboxaldehyde by HPLC. In a preferred embodiment of the present invention, the crude product is crystallized from ethanol to get substantially pure 2-acetyl-3-benzofurazan-4-yl-acrylic acid methyl ester as it allows for obtaining better yields.

In the second step, 2-acetyl-3-benzofurazan-4-yl-acrylic acid methyl ester is reacted with isopropyl-β-aminocrotonate in ethanol at 25 to 40° C. and preferably at 25 to 35° C. In this reaction isopropyl-β-aminocrotonate 0.9 to 1.05 mol is used for every 1.0 mol of 2-acetyl-3-benzofurazan-4-yl-acrylic acid methyl ester, preferably 0.95 to 1.0 mol is used for every 1.0 mol of 2-acetyl-3-benzofurazan-4-yl-acrylic acid methyl ester. This reaction goes to the completion in 6 to 8 hr at 30° C. Ethanol is removed from the reaction mixture at less than 50° C. under vacuum to get the concentrate containing Isradipine. The concentrate is dissolved in ethyl acetate and washed with water to remove a little amount of the unknown water soluble impurities formed in this reaction. The water washed ethyl acetate layer is then concentrated at less than 50° C. under reduced pressure. The concentrate is then dissolved in ethanol at 65 to 80° C. and cooled to get the Isradipine crystallised from the solution. The product is optionally recrystallised from ethanol to get pure Isradipine having typical purity more than 99.4% and the impurity (III) less than 0.3% and impurity (IV) less than 0.2% and other unknown impurity total less than 0.1% by HPLC analysis.

The present invention will now be described in more detail by way of examples, which should not be construed as limiting the invention thereto.

EXAMPLE 1

Preparation of 2-acetyl-3-benzofurazan-4-yl-acrylic acid methyl ester

Suspended 2,1,3-benzoxadiazole-4-carboxaldehyde (50 g, 0.33 mote) in diisopropyl ether (1300 ml) and added methyl acetoacetate (38 g, 0.32 mole), piperidine (2 g) glacial acetic acid (6 g) in to the suspension one after another. Refluxed the reaction mixture at 70° C. with continuous water separation. Removed sample from the reaction mixture and analysed the samples by qualitative HPLC. Washed the reaction mixture with hydrochloric acid (~3.5 wt %, 250 ml, sodium bicarbonate solution (~10 wt %, 250 ml and water (250 ml, 100 ml. Dried the organic layer over sodium sulphate (25 g) and then distilled diisopropyl ether under vacuum to get crude 2-acetyl-3-benzofurazan-4-yl-acrylic acid methyl ester (yield 70 g, HPLC purity 93.4%).

EXAMPLE 2

Purification of 2-acetyl-3-benzofurazan-4-yl-acrylic acid methyl ester

Added diisopropyl ether (100 ml) in to the concentrate containing crude 2-acetyl-3-benzofurazan-4-yl-acrylic acid methyl ester (70 g) as obtained in Example 1, and heated to 50° C. and then cooled to 30° C. and filtered. The product washed with diisopropyl ether and repurified from diisopropyl ether and dried at 40° C. under vacuum to obtain 50 g tided product (yield=61%, purity 99.2%, and 0.12% 2,1,3-benzoxadiazole-4-carbaxaldehyde by HPLC)

EXAMPLE 3

Purification of 2-acetyl-3-benzofurazan-4-yl-acrylic acid methyl ester

Added ethanol (160 ml) into the concentrate containing crude 2-acetyl-3-benzofurazan-4-yl-acrylic acid methyl ester (70 g) as obtained in Example 1, and heated to 45 to 50° C. and stirred for 30 minutes. The content is then cooled to 0 to 5° C. and filtered, the product washed with chilled ethanol (20 ml). The product is dried at 4.0° C. under vacuum to obtain 63 g titled product (2,1,3-benzoxadiazole-4-carbaxaldehyde content is 0.21% by HPLC)

EXAMPLE 4

Preparation of Isradipine using crude 2-acetyl-3-benzofurazan-4-yl-acrylic acid methyl ester Dissolved the crude 2-acetyl-3-benzofurazan-4-yl-acrylic acid methyl ester obtained in example—1 (25 g, 0.10 mol) in absolute ethanol (375 ml) and added in to the solution isopropyl-β-aminocrotonate (13.15 ml, 0.09 mol). Stirred the reaction mixture under nitrogen atmosphere at 25-28° C. for 7 hr. Removed sample from the reaction mixture and analysed the sample by qualitative HPLC. Distilled ethanol from the reaction mixture under vacuum at 50° C. Dissolved the residue in ethyl acetate (235 ml) and washed twice with water (90 ml). Dried the organic layer over sodium sulphate and distillation under vacuum at 50° C. Dissolved the concentrate in ethanol (65 ml) at 70° C. and slowly cooled to 5° C. to get the product crystallised. Filtered the product and washed with pre cooled ethanol (25 ml). Recrystallised the product from ethanol (60 ml) and dried at 70° C. under vacuum to obtain Isradipine (yield=20 g, purity=98.2% and Impurity III=0.64%, Impurity IV=0.51% by HPLC)

EXAMPLE 5

Preparation of Isradipine using purified 2-acetyl-3-benzofurazan-4-yl-acrylic acid methyl ester Dissolved 2-acetyl-3-benzofurazan-4-yl-acrylic acid methyl ester (25 g, 0.10 mol in absolute ethanol (375 ml) and added in to the solution isopropyl-β-aminocrotonate (13.15 ml, 0.09 mol). Stirred the reaction mixture under nitrogen atmosphere at 25-28° C. for 5 hr. Removed sample from the reaction mixture and analysed the sample by qualitative HPLC. Distilled ethanol from the reaction mixture under vacuum at 50° C. Dissolved the residue in ethyl acetate (235 ml) and washed twice with water (90 ml). Dried the organic layer over sodium sulphate and distillation under vacuum at 50° C. Dissolved the concentrate in ethanol (65 ml) at 70° C. and slowly cooled to 5° C. to get the product crystallised. Filtered the product and washed with pre cooled ethanol (25 ml). Recrystallised the product from ethanol (60 ml) and dried at 70° C. under vacuum to obtain 25 g Isradipine (yield=67%, purity 99.5%, Impurity III=0.20%, and Impurity IV=0.12% by HPLC)

EXAMPLE 6

Preparation of Isradipine using purified 2-acetyl-3-benzofurazan-4-yl-acrylic acid methyl ester Dissolved the purified 2-acetyl-3-benzofurazan-4-yl-acrylic acid methyl ester obtained in example—3 (25 g, 0.10 mol) in absolute ethanol (375 ml) and added in to the solution isopropyl-β-aminocrotonate (13.15 ml, 0.09 mol). Stirred the reaction mixture under nitrogen atmosphere at 25-28° C. for 5 hr. Removed sample from the reaction mixture and analysed the sample by qualitative HPLC. Distilled ethanol from the reaction mixture under vacuum at 50° C. Dissolved the residue in ethyl acetate (235 ml) and washed twice with water (90 ml). Dried the organic layer over sodium sulphate and distillation under vacuum at 50° C. Dissolved the concentrate in ethanol (65 ml at 70° C. and slowly cooled to 5° C. to get the product crystallised. Filtered the product and washed with pre cooled ethanol (25 ml and dried at 70° C. under vacuum to obtain 30 g Isradipine (purity=99.4%, Impurity III=0.22%, and Impurity IV=0.11% by HPLC.

Throughout this application, various publications are referenced. The disclosures of these publications in their entireties are hereby incorporated by reference into this application in order to more fully describe the state of art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An improved method for the manufacture of 4-(4-Benzofuranzanyl)-1,4-dihydro-2,6-dimethyl-3,5-pyridinedicarboxylic acid methyl 1-methylethyl ester comprising the steps of:
   (i) reacting 2,1,3-benzoxadiazole-4-carboxaldehyde with methyl acetoacetate in the presence of acetic acid and piperidine in diisopropyl ether to obtain 2-acetyl-3-benzofurazan-4-yl-acrylic acid methyl ester;
   (ii) isolating and purifying 2-acetyl-3-benzofuran-4-yl-acrylic acid methyl ester to obtain purified 2-acetyl-3-benzofuran-4-yl-acrylic acid methyl ester by recrystallizaton from a solvent;
   (iii) reacting 2-acetyl-3-benzofuran-4-yl-acrylic acid methyl ester with isopropyl-β-aminoacrotonate in ethanol to obtain 4-(4-Benzofuranzanyl)-1,4-dihydro-2,6-dimethyl-3,5-pyridinedicarboxylic acid methyl 1-methylethyl ester.

2. An improved process as claimed in claim 1 wherein step (iii) is carried out at 25 to 40° C.

3. An improved process as claimed in claim 2 wherein step (iii) is carried out at 25 to 35° C.

4. An improved process as claimed in claim 1 wherein about 0.9 to 1.1 mol of methyl acetoacetate is used for every 1.0 mol of 2,1,3-benzoxadiazole-4-carboxaldehyde.

5. An improved process as claimed in claim 4 wherein about 0.95 to 1.0. mol of methyl acetoacetate is used for every 1.0 mol of 2,1,3-benzoxadiazole-4-carboxaldehyde.

6. An improved process as claimed in claim 1 wherein acetic acid and piperidine are used in catalytic amount.

7. An improved process as claimed in claim 6 wherein about 0.25 to 3.0 mol of acetic acid and about 0.8 to 0.06 mol of piperidine is used for every 1 mol of 2,1,3-benzoxadiazole-4-carboxaldehyde.

8. An improved process as claimed in claim 1 wherein the 2-acetyl-3-benzofurazan-4-yl-acrylic acid methyl ester obtained in step (ii) is crystallized from diisopropyl ether to obtain pure 2-acetyl-3-benzofurazan-4-yl-acrylic acid methyl ester.

9. An improved process as claimed in claim 1 wherein about 0.9 to 1.05 mol of isopropyl-β-aminocrotonate is used for every 1 mol of 2-acetyl-3-benzofurazan-4-yl-acrylic acid methyl ester.

10. An improved process as claimed in claim 9 wherein about 0.9 to 1.00 mol of isopropyl-β-aminocrotonate is used for every 1 mol of 2-acetyl-3-benzofurazan-4-yl-acrylic acid methyl ester.

11. An improved process as claimed in claim 1 wherein the solvent is selected from the group consisting of an ether, an alcohol and a mixture thereof.

* * * * *